(12) United States Patent
Halmann et al.

(10) Patent No.: US 8,414,495 B2
(45) Date of Patent: Apr. 9, 2013

(54) ULTRASOUND PATCH PROBE WITH MICRO-MOTOR

(75) Inventors: Menachem (Nahi) Halmann, Milwaukee, WI (US); Mirsaid Seyed-Bolorforosh, Guilderland, NY (US); Syed Ishrak, Foxpoint, WI (US); David Mills, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 693 days.

(21) Appl. No.: 12/208,090

(22) Filed: Sep. 10, 2008

(65) Prior Publication Data

US 2010/0063398 A1 Mar. 11, 2010

(51) Int. Cl.
*A61B 8/00* (2006.01)

(52) U.S. Cl.
USPC .......................................................... 600/459

(58) Field of Classification Search .................. 600/459, 600/466, 467, 462; 367/140, 153, 154; 73/618, 73/634; 310/98, 40 R
See application file for complete search history.

(56) References Cited

U.S. PATENT DOCUMENTS

| 5,720,285 | A | * | 2/1998 | Petersen | 600/459 |
| 5,957,846 | A | * | 9/1999 | Chiang et al. | 600/447 |
| 7,494,469 | B2 | * | 2/2009 | Bruestle | 600/459 |
| 7,666,143 | B2 | * | 2/2010 | Wilser et al. | 600/463 |

* cited by examiner

*Primary Examiner* — Parikha Mehta
(74) *Attorney, Agent, or Firm* — The Small Patent Law Group; Dean D. Small

(57) ABSTRACT

An ultrasound probe for guidance procedures is provided. The ultrasound probe includes a linear transducer array and a micro-motor configured to mechanically move the linear transducer array to provide ultrasound guidance of procedures.

14 Claims, 11 Drawing Sheets

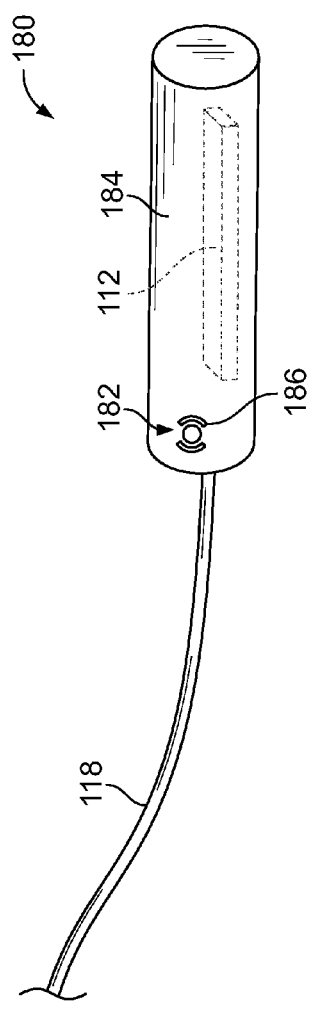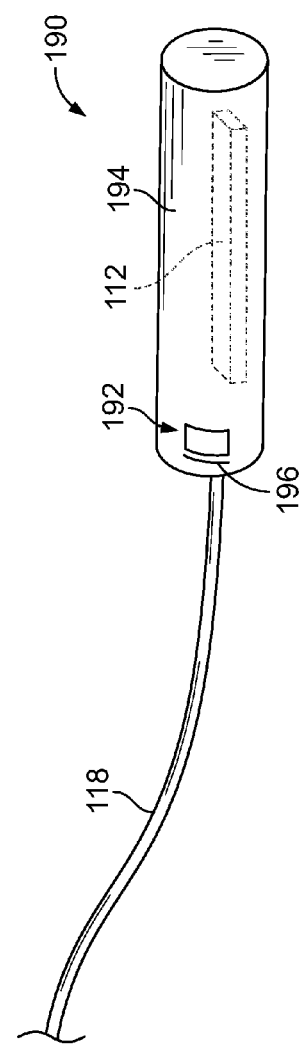

ULTRASOUND PATCH PROBE WITH MICRO-MOTOR

BACKGROUND OF THE INVENTION

This invention relates generally to ultrasound systems and, more particularly to a medical ultrasound imaging systems, especially for guidance procedures.

Ultrasound systems are configured to connect to an ultrasound scanning device to perform an ultrasound scan. Depending on the type of ultrasound scan to be performed, a probe having a particular transducer arrangement may be used that allows for performing the specific ultrasound scan (e.g., imaging of a specific volume or body). The ultrasound system usually includes a control portion (e.g., a control console or portable unit) that provides interfaces for receiving user inputs. For example, different buttons, knobs, etc. are provided to allow a user to select different options and control the scanning of an object using the connected ultrasound probe.

Mechanical volumetric probes are known and allow acquisition of real-time volumes of interest (as opposed to a field of view within a single two-dimensional plane). Mechanical volumetric probes operate based on mechanical movement of an electronic one-dimensional array to form an image by mechanically scanning in one direction and electronically scanning along an orthogonal axis. A two-dimensional volumetric probe is steered electronically in two orthogonal axes to acquire an image of a volume. These volumetric probes are typically used in obstetrical/gynecological and cardiac applications because of the real-time capabilities of these probes to provide three-dimensional images. However, these probes are not optimized and do not often operate satisfactorily for imaging during guidance procedures. Moreover, most volumetric probes are relatively large and heavy, making scanning with these probes sometimes cumbersome when held by the user during a scan or examination.

Ultrasound guided interventional procedures are common in foliations such as breast biopsies, vascular access (e.g., placing of central line catheters), vein closure procedures and regional nerve blocks, among others. During these procedures, a physician (or nurse) has to hold the ultrasound probe, which is a non-volumetric probe, in one hand and a needle in the other hand to perform the procedure, while observing the ultrasound image in real-time. However, in many cases, this type of procedure requires two individuals including an operator performing the scanning and another physician performing the guidance procedure. In other cases, no guidance is used.

Thus, using known ultrasound systems it is difficult to perform ultrasound imaging in combination with interventional guidance procedures. Moreover, volumetric imaging is not optimized for such interventional guidance procedures.

BRIEF DESCRIPTION OF THE INVENTION

In accordance with an embodiment of the invention, an ultrasound probe is provided. The ultrasound probe includes a linear transducer array and a micro-motor configured to mechanically move the linear transducer array to provide ultrasound guidance of procedures.

In accordance with another embodiment of the invention an ultrasound system is provided. The ultrasound system includes a host system and a volumetric ultrasound probe communicatively coupled to the host system. The volumetric ultrasound probe is configured to attach to a skin of a person.

In accordance with yet another embodiment of the invention, a disposable sterile module for attachment to an ultrasound probe is provided. The disposable sterile module includes a flexible body having an ultrasound gel section that includes a pre-applied amount of acoustic gel. The disposable sterile module further includes at least one adhesive section on the flexible body.

BRIEF DESCRIPTION OF THE DRAWINGS

FIG. 8 is a perspective view of an ultrasound probe having a miniaturized trackball formed in accordance with an embodiment of the invention.

FIG. 9 is a perspective view of an ultrasound probe having a miniaturized touch-pad formed in accordance with an embodiment of the invention.

DETAILED DESCRIPTION OF THE INVENTION

Figure 1:
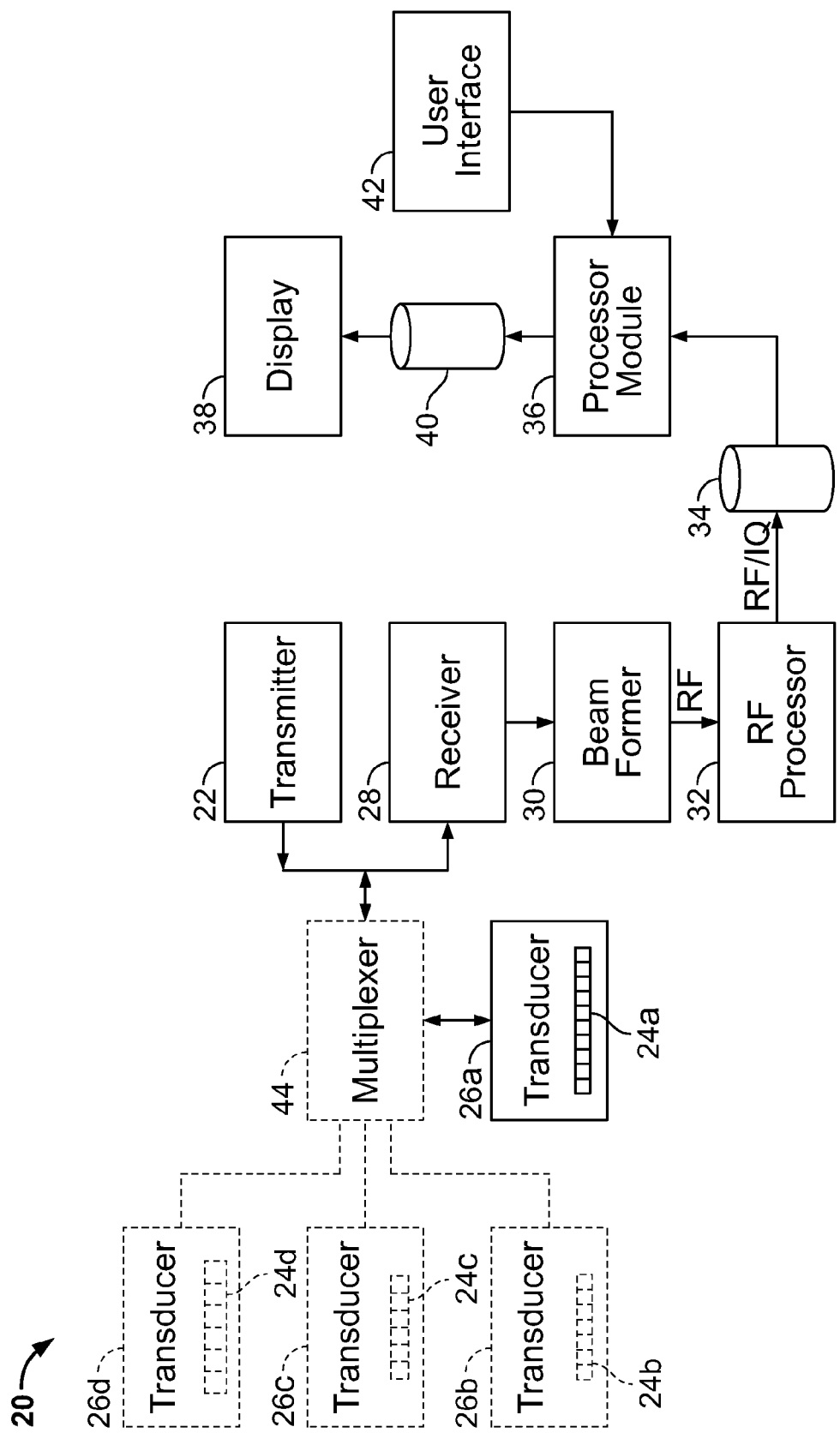
FIG. 1 is a block diagram of an ultrasound system formed in accordance with an embodiment of the invention.

The foregoing summary, as well as the following detailed description of certain embodiments of the invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although the various embodiments may be described in connection with an ultrasound system, the methods and systems described herein are not limited to ultrasound imaging. In particular, the various embodiments may be implemented in connection or combination with different types of medical imaging, including, for example, magnetic resonance imaging (MRI) and computed-tomography (CT) imaging. Further, the various embodiments may be implemented in other non-medical imaging systems, for example, non-destructive testing systems, such as airport screening systems.

Various embodiments of the invention provide a miniaturized volumetric ultrasound probe that may be used, for example, in ultrasound guidance interventional procedures, such as biopsies, adult vascular access, neonate vascular access, regional nerve blocks for anesthesia, among others. As used herein, miniaturized probe means smaller than conventional ultrasound probes, which in some embodiments refers to a probe that has a size and weight allowing the probe to be attached to, for example, a person's skin such that both hands of the physician are free to perform a guided interventional procedure.

FIG. 1 is a block diagram of an exemplary ultrasound system 20 in which various embodiments of a miniaturized ultrasound probe may be used to perform ultrasound imaging as described in more detail below. The ultrasound system 20 includes a transmitter 22 that drives an array of elements 24 (e.g., piezoelectric crystals) within one or more transducers 26 to emit pulsed ultrasonic signals into a body or volume. In the illustrated embodiment, the transmitter 22 at least drives an array of elements 24a in a transducer 26a and optionally drives one or more of an array of elements 24b-24d in transducers 26b-26d. When optionally driving more than one array of elements 24 in more than one corresponding transducer 26 a multiplexer 44 is provided to control which of the one or more array of elements 24 and/or transducers 26 is driven, including the specific elements within a particular array of elements 24. The array of elements 24 may have multiple rows of elements, for example, two rows, three rows, or higher. The number of elements in the array of elements 24 also may be changed. For example, the array of elements 24 may include three rows of elements with each row having 128 elements. Thus, the array of elements 24 may be any type of array, for example, a 1.5D or 1.25D array. Also, the multiplexer 44 and other switching circuitry may be provided with the housing of the ultrasound probe.

It should be noted that with respect to the arrays of elements 24a-24d in the transducers 26a-26d, a variety of different geometries and configurations may be used and the transducers 26a-26d may be provided as part of, for example, different types of ultrasound probes as described in more detail below. However, in some embodiments, one or more of the transducer 26a-26d is configured having the same geometry, for example, the same size or configuration and may be part of the same type of ultrasound probe.

The emitted ultrasonic signal are back-scattered from structures in the body, for example, blood cells, muscular tissue, veins or objects within the body (e.g., a catheter or needle) to produce echoes that return to the array of elements 24. The echoes are received by a receiver 28, which optionally are multiplexed through the multiplexer 44 when using more than one transducer 26a-26d and corresponding array of elements 24a-24d. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs), which may be acquired from more than one ultrasound probe, and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis and analysis, as well as for use, for example, during an ultrasound guided interventional procedure. The display 38 may automatically display, for example, a 3D or 4D ultrasound data set stored in the memory 34 or 40 or currently being acquired. One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by moving the transducer 26, such as along a linear or arcuate path, while scanning a region of interest (ROI) or by placing a plurality of transducers 26 at different orientations with respect to the ROI, for example, by attaching a plurality of ultrasound probes to a patient's skin as described in more detail below. At each linear or arcuate position, the transducer 26 obtains scan planes that are stored in the memory 34. The transducer 26 also may be mechanically moveable within the ultrasound probe to acquire volumetric ultrasound images.

Figure 2:
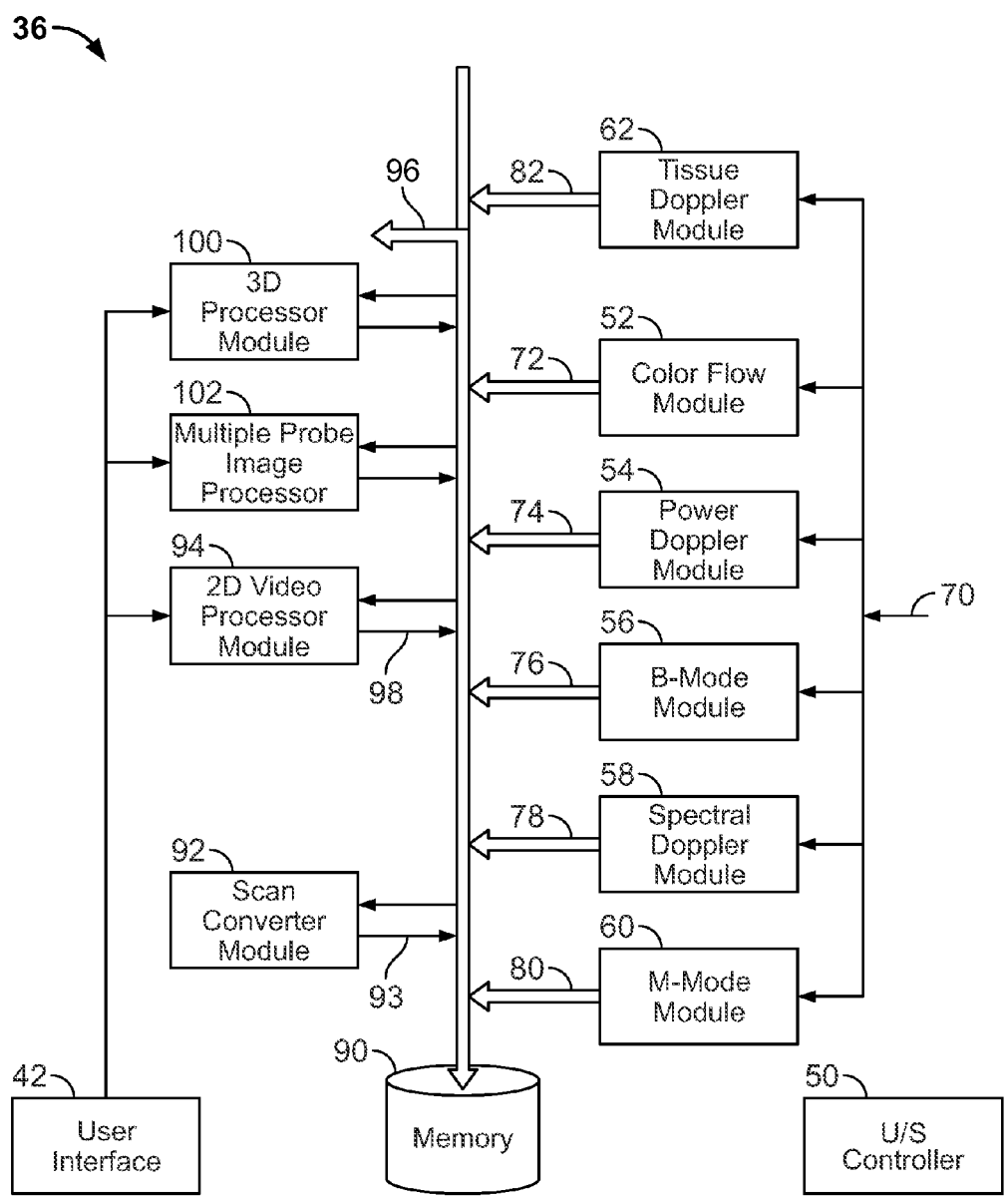
FIG. 2 is a block diagram of an ultrasound processor module of FIG. 1 formed in accordance with an embodiment of the invention.

FIG. 2 is an exemplary block diagram of the ultrasound processor module 36 of FIG. 1. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the-shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-62 perform mid-processor operations. The ultrasound processor module 36 may receive ultrasound data 70 in one of several forms. In the embodiment of FIG. 2, the received ultrasound data 70 constitutes IQ data pairs representing the real and imaginary components associated with each data sample. The IQ data pairs are provided to one or more sub-modules, for example, a color-flow sub-module 52, a power Doppler sub-module 54, a B-mode sub-module 56, a spectral Doppler sub-module 58 and an M-mode sub-module 60. Other sub-modules may be included, such as a Tissue Doppler (TDE) sub-module 62, among others.

Each of sub-modules 52-62 are configured to process the IQ data pairs in a corresponding manner to generate color-flow data 72, power Doppler data 74, B-mode data 76, spectral Doppler data 78, M-mode data 80, and tissue Doppler data 82, among others, all of which may be stored in a memory 90 (or memory 34 or image memory 40 shown in FIG. 1) temporarily before subsequent processing. The data 72-82 may be stored, for example, as sets of vector data values, where each set defines an individual ultrasound image frame. The vector data values are generally organized based on the polar coordinate system.

A scan converter sub-module 92 accesses and obtains from the memory 90 the vector data values associated with an image frame and converts the set of vector data values to Cartesian coordinates to generate an ultrasound image frame 93 formatted for display. The ultrasound image frames 93 generated by the scan converter sub-module 92 may be provided back to the memory 90 for subsequent processing or may be provided to the memory 34 or the image memory 40.

Once the scan converter sub-module 92 generates the ultrasound image frames 93 associated with the data, the image frames may be restored in the memory 90 or communicated over a bus 96 to a database (not shown), the memory 34, the image memory 40 and/or to other processors (not shown).

As an example, it may be desired to view different ultrasound images relating to an invasive procedure in real-time on the display 38 (shown in FIG. 1). To do so, the scan converter sub-module 92 obtains data sets for images stored in the memory 90 or that are currently being acquired, which may be acquired from multiple ultrasound probes. The vector data is interpolated where necessary and converted into an X,Y format for video display to produce ultrasound image frames. The scan converted ultrasound image frames are provided to a display controller (not shown) that may include a video processor that maps the video to a gray-scale mapping for video display. The gray-scale map may represent a transfer function of the raw image data to displayed gray levels. Once the video data is mapped to the gray-scale values, the display controller controls the display 38, which may include one or more monitors or windows of the display, to display the image frame. The image displayed in the display 38 is produced from an image frame of data in which each datum indicates the intensity or brightness of a respective pixel in the display.

Referring again to FIG. 2, a 2D video processor sub-module 94 may be used to combine one or more of the frames generated from the different types of ultrasound information or from different ultrasound probes. For example, the 2D video processor sub-module 94 may combine different image frames by mapping one type of data to a gray map and mapping the other type of data to a color map for video display. In the final displayed image, the color pixel data is superimposed on the gray scale pixel data to form a single multi-mode image frame 98 that is again re-stored in the memory 90 or communicated over the bus 96. Successive frames of images may be stored as a cine loop (4D images) in the memory 90 or memory 40 (shown in FIG. 1). The cine loop represents a first in, first out circular image buffer to capture image data that is displayed in real-time to the user. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three-dimensional image representations thereof, such as through volume rendering or surface rendering algorithms as are known. The three-dimensional images may be generated utilizing various imaging techniques, such as ray-casting, maximum intensity pixel projection and the like.

A multiple probe image processor 102 also may be controlled by the user interface 42 and accesses the memory 90 to obtain groups of ultrasound image frames that have been stored or that are currently being acquired by more than one ultrasound probe and to generate three dimensional image representations thereof, which may show different views of an invasive device along with an image of an ROI. The three-dimensional images may be generated utilizing various imaging techniques, such as ray-casting, maximum intensity pixel projection and the like. The images may be displayed using volume rendering or surface rendering algorithms as are known. The images from the different ultrasound probes may be displayed on a single screen (e.g., concurrent side by side display) or a user can switch between the images, for example, alternately between the images. Optionally, the images from different ultrasound probes may be combined, for example, superimposed on a single display.

Figure 3:
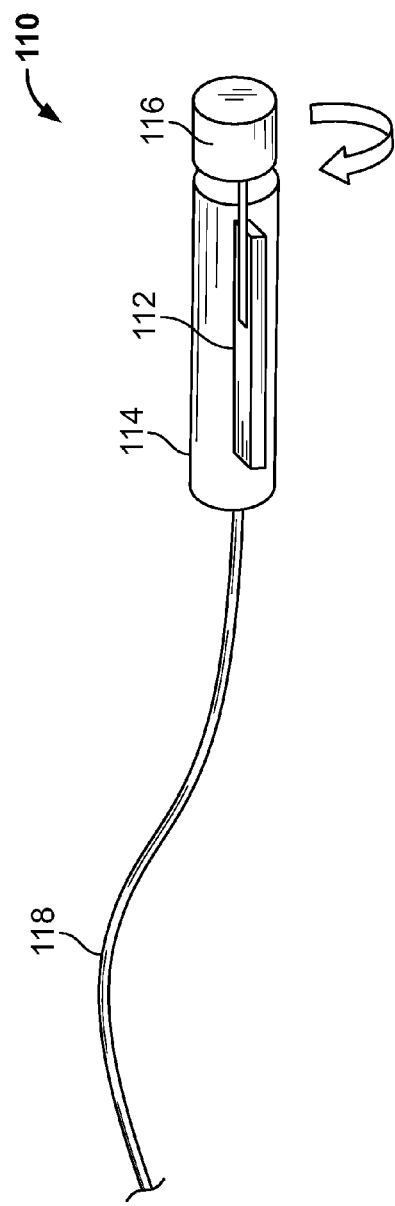
FIG. 3 is a perspective view of an ultrasound probe formed in accordance with an embodiment of the invention.
Figure 4:
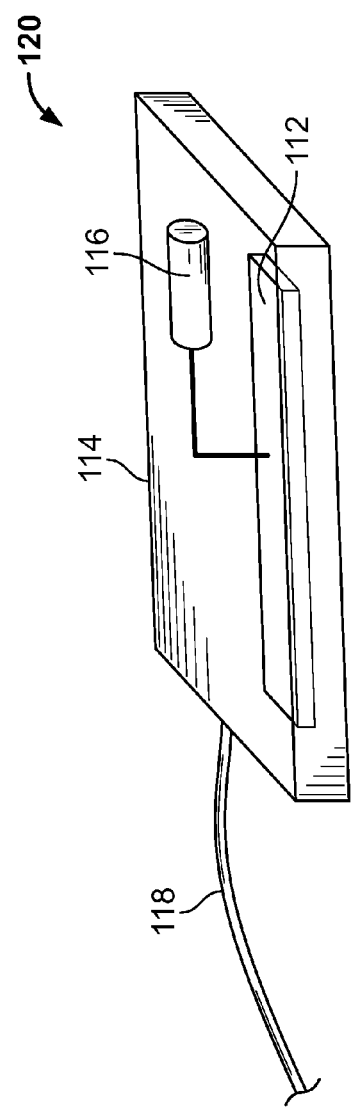
FIG. 4 is a perspective view of an ultrasound probe formed in accordance with another embodiment of the invention.

Various embodiments of the invention provide miniaturized ultrasound probes, such as the ultrasound probe 110 shown in FIG. 3 and the ultrasound probe 120 shown in FIG. 4, which are simplified illustrations of the ultrasound probes 110 and 120. In particular, the ultrasound probe 110 includes a linear transducer array 112 (e.g., a one-dimensional or two-dimensional array), which is a smaller array (e.g., dimensionally smaller). The linear transducer array 112 is provided within a probe housing 114 such that the linear transducer array 112 in one embodiment is configured to rotate around a longitudinal axis of the ultrasound probe 110 as illustrated by the arrow in FIG. 3. In the illustrated embodiment, the probe housing 114 has a cylindrical shape to allow the linear transducer array 112 to rotate therein. It should be noted that the linear transducer array 112 may be differently shaped and sized, for example, to include different numbers of elements or rows of elements as desired or needed. Moreover the linear transducer array 112 may rotate in different directions, for example, in one embodiment the linear transducer array 112 rotates normal to the face of the ultrasound probe instead of normal to the side of the probe.

The linear transducer array 112 is coupled to and driven by a micro-motor 116. For example, the micro-motor 116 may be a miniaturized motor such as a brushless DC motor with integrated electronics available from Maxon Precision Motors (e.g., EC-1 line of motors), which range in diameter from 6-90 millimeters (mm) and can provide up to 90 watts of power. Other examples of micro-motors 116 that may be used include, but are not limited to the DC-Micromotor Series 1224 available from the Faulhaber Group having a diameter of 12 mm in one version, a miniature stepper motor available from Arsape or a miniature motor from a Danaher Motion Company. However, it should be appreciated that the micro-motor 116 is not limited to the above-identified motors, but other motors may be used that provide the smaller size and weight of the ultrasound probes as described herein.

The ultrasound probe 110 also includes a probe cable 118. The probe cable 118 provides connection to a host system that controls the operation of the ultrasound probe 110 to acquire ultrasound images. For example, the probe cable 110 can allow connection of the ultrasound probe 110 to the ultrasound system 20 (shown in FIG. 1).

The various embodiments are not limited to ultrasound probes having a particular shape or configuration. Accordingly, the probe housing 114 may be shaped and configured differently. For example, as shown in FIG. 4, the ultrasound probe 120 is rectangular in shape or cross-section (e.g., matchbox shaped), which may be configured as a patch type ultrasound probe configured for attachment to a patient's skin as described in more detail herein and shown in use in FIG. 7. In the various embodiments, like reference numeral represent like part, although not necessarily identical parts.

It should be noted that various embodiments are not limited to linear transducer arrays 112 that are mechanically movable. The linear transducer array 112 may be mounted in a fixed position and orientation within the probe housing 114. In such an embodiment, no micro-motor 116 is included. Also, the linear transducer array 112 may be a two-dimensional array that is electronically steered using any known method.

Figure 5:
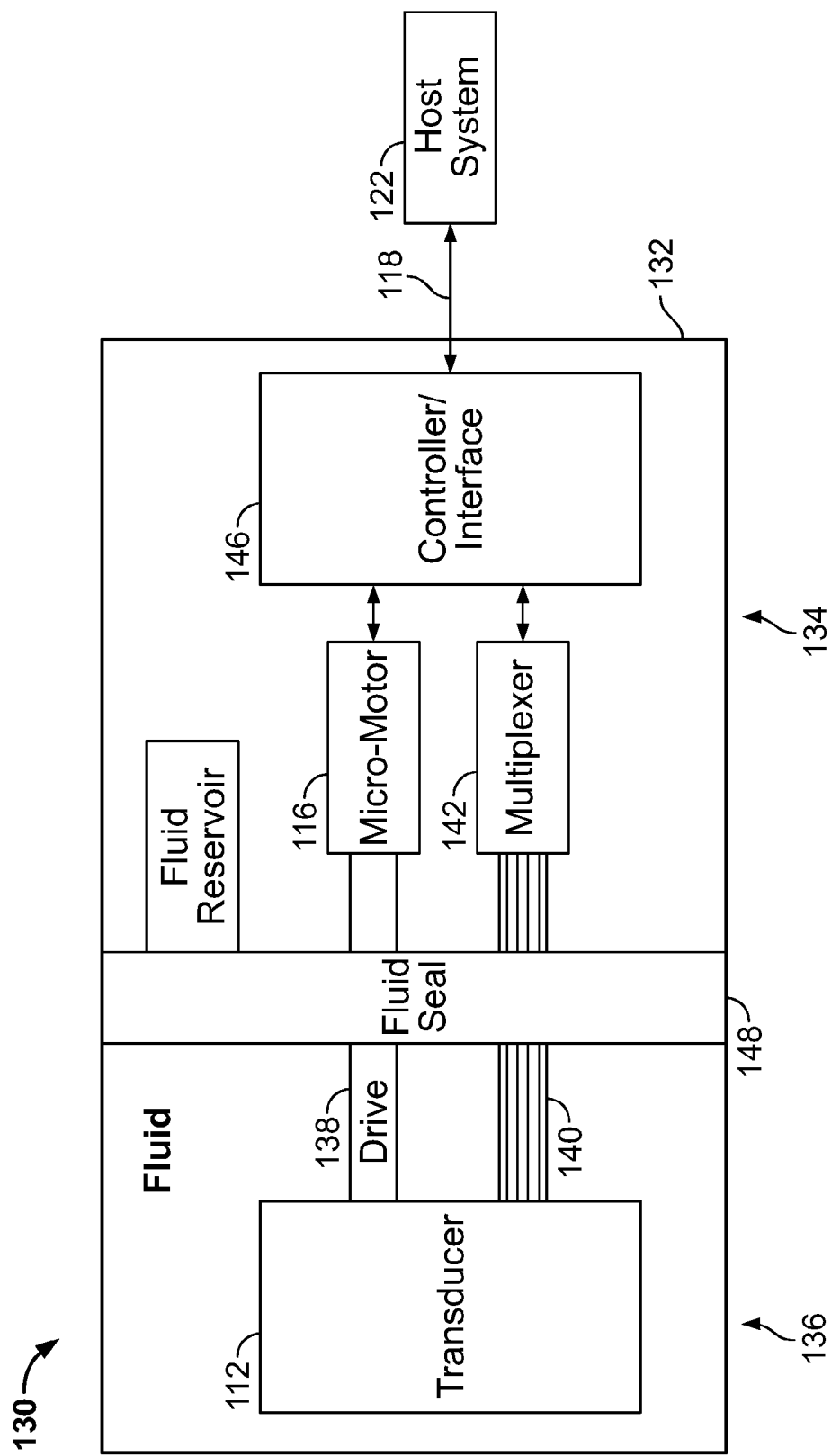
FIG. 5 is a block diagram of an ultrasound probe formed in accordance with an embodiment of the invention.

A more detailed block diagram of an ultrasound probe 130 is shown in FIG. 5, which is a mechanical volumetric or volume imaging probe having the linear transducer array 112, which may be, for example, the array of elements 24 (shown in FIG. 1). The ultrasound probe 130 is in communication with a host system 122 (e.g., ultrasound scanner or ultrasound laptop) via the probe cable 118. The host system 122 may include some or all of the components of the ultrasound system 20 (shown in FIG. 1), including the multiplexer 44 to control more than one ultrasound probe. The probe 130 includes a housing 132 having a first chamber 134 (e.g., a dry chamber) and a second chamber 136 (e.g., a wet chamber). The first chamber 134 and second chamber 136 may be formed as a single unit (e.g., unitary construction) or may be formed as separate units connected together. In an exemplary embodiment, the first chamber 134 is a dry or air chamber having contained therein drive means for mechanically controlling the linear transducer array 112 and communication means for electrically controlling the linear transducer array 112.

The drive means generally includes the micro-motor 116 (e.g., stepper motor) as described herein and a drive 138, which may include, for example, a gear arrangement, such as a single axle or a two-stage gear arrangement having a belt drive and a rope drive. The communication means generally includes one or more communication lines, for example, configured as one or more flexible printed circuit boards 140 that connect at one end to the probe cable 118 through a multiplexer 142 and a controller/interface 146, and at the other end to the linear transducer array 112. The communication means thereby provides communication between the linear transducer array 112 and the host system 122.

It should be noted that although the drive means and communication means are described herein having specific component parts, the drive means and communication means are not so limited. For example, the drive means may have a different gear arrangement and the communication means may have different connection members or transmission lines.

In this exemplary embodiment, the second chamber 136 is a wet chamber (e.g., chamber having acoustic liquid therein) having contained therein transducer driving means for moving (e.g., rotating or swinging) the linear transducer array 112 and transducer control means for selectively driving elements of the linear transducer array 112 (e.g., the piezoelectric ceramics). The transducer driving means generally includes the drive 138 that may be connected to a scan head housing (not shown) supported, for example, on brackets (not shown), that operates to move the linear transducer array 112 as part of a scan head when driven by the drive means. A support member (not shown) also may be provided for supporting the scan head housing and a biasing spring (not shown) may be provided, for example, to ensure proper tension on the drive means and transducer drive means. It should be noted that an acoustic membrane (not shown) may be provided surrounding the scan head housing and formed as part of the housing thereof.

The transducer control means generally includes one or more flexible printed circuit boards 140, and optionally the multiplexer 142 connected to the linear transducer array 112. The communication means are connected to the transducer driving means using any suitable connector, such as a complimentary pin connector arrangement. It should be noted that the various components also may be miniaturized or allow for the smaller size of the ultrasound probe 130. For example, the multiplexer 142 may be one or more multiplexer boards having on-board or integrated multiplexing circuits or chips, such as an analog multiplexer or switch IC available from Super-Tex Inc. (e.g., HV2XX or HV2XXX line of multiplexing boards).

It also should be noted that although the transducer driving means and transducer control means are described herein having specific component parts, the transducer driving means and the transducer control means are not so limited. For example, the transducer driving means may have a different shaft arrangement and the transducer control means may have different control circuits or transmission lines. It also should be noted that additional or different component parts may be provided in connection with the probe 130 as needed or desired, and/or based upon the particular type and application of the probe 130.

It should be noted that one or more seals members 148 may be provided between the first chamber 134 and the second chamber 136 to provide a liquid tight sealing arrangement between the first chamber 134 and second chamber 136. Different configurations of sealing arrangements are contemplated. For example, one or more slots or openings (not shown) may be provided as part of a bracket member (not shown) with the seal member 148 (e.g., rubber gasket and aluminum plate) ensuring proper sealing between the first chamber 134 and second chamber 136.

In operation, and as described in more detail herein, the multiplexer 44 can control the communication of signals to one or more transducers 26a-26d, which may be provided as part of one or more ultrasound probes 130, to both control the mechanical movement and electrical activation of the linear transducer array 112 of each of the probes 130, as well as the selection of which one or ones of the ultrasound probes 130 are active and acquiring images. It should be noted that the linear transducer array 112 may be configured to operate in different modes, such as, for example, a 1D, 1.25D, 1.5D, 1.75D, 2D, 3D and 4D modes of operation.

Accordingly, the various embodiments of ultrasound probes described herein are miniaturized and provide volumetric imaging. For example, the entire probe in some embodiments weighs less than 100 grams and has a volume of less than 15,000 mm$^3$. The various embodiments of ultrasound probes, because of the miniaturized design, may be for example, attached to a person's skin during scanning operation. During such uses, the various embodiments may provide a disposable sterile module 150 that is used in combination with the ultrasound probe 110 or 120 (the ultrasound probe 110 is shown). The disposable sterile module 150 generally provides an ultrasound gel, adhesive element and a sterile sleeve for the probe cable 118.

Figure 6:
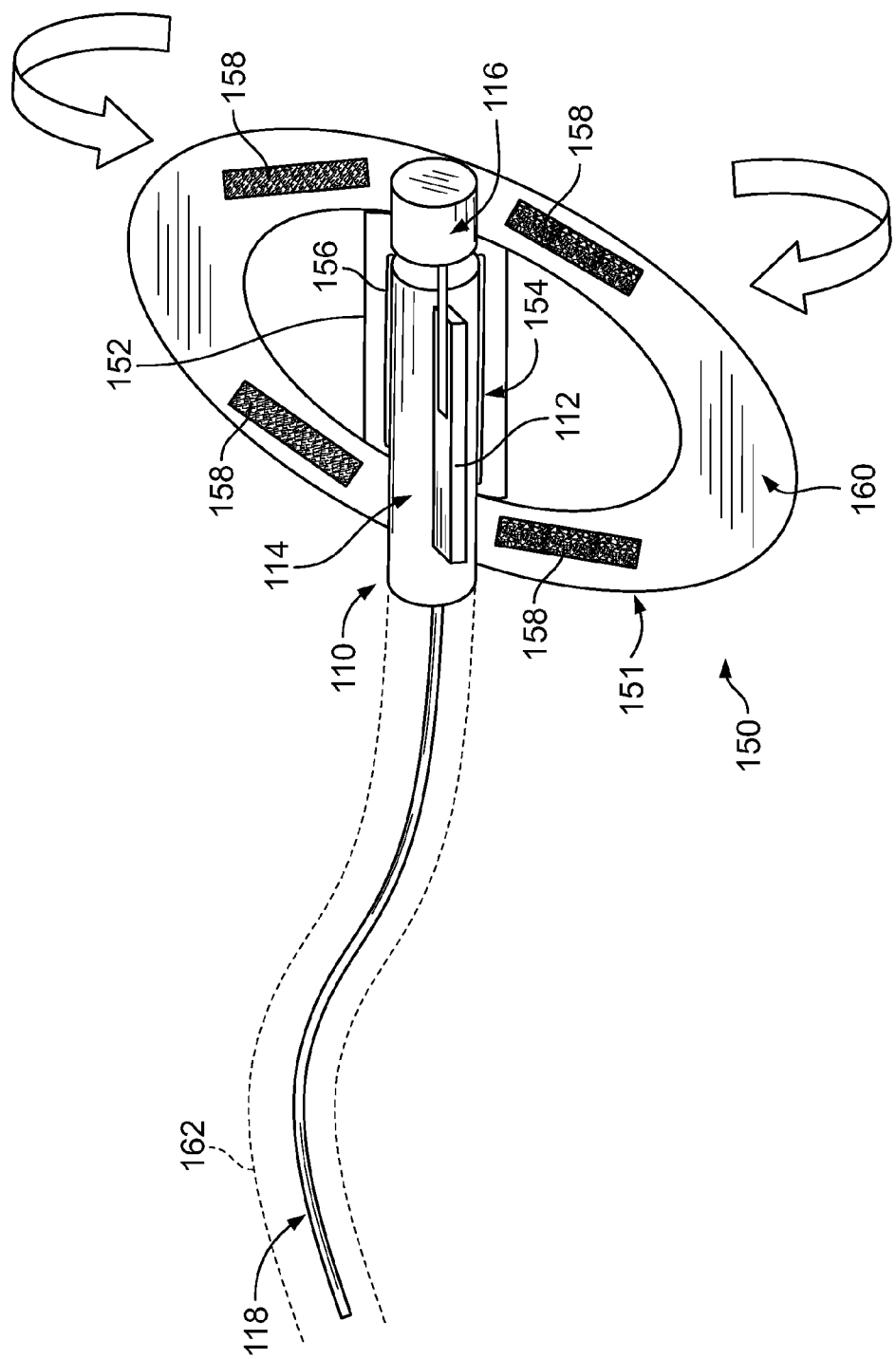
FIG. 6 is a drawing illustrating a disposable sterile module formed in accordance with an embodiment of the invention.

In the illustrated embodiment of FIG. 6, the disposable sterile module 150 includes a generally ring-shaped body 151 (which may be formed, for example, from rubber or other flexible material) with a probe contact section 152 extending from one side of the ring-shaped body 151 to the other side of the ring-shaped body 151 and that abuts the imaging portion of the ultrasound probe 110, for example, adjacent the linear transducer array 112. The probe contact section 152 includes an ultrasound gel section 154 that has a pre-applied amount of acoustic gel 156. The amount of acoustic gel 156 may be different, for example, based on the type of scan to be performed, the type of ultrasound probe, etc. The disposable sterile module 150 also includes one or more adhesive sections 158. Any type of adhesive material or substance may be used to form the adhesive sections 158, for example, a skin adhesive or a two-sided medical tape.

The disposable sterile module 150 also includes one or more handling areas 160, which may generally define handle shaped portions of the disposable sterile module 150. The one or more handling areas 160 may be folded as illustrated by the arrows in FIG. 6 such that the handling areas 160 fold up to provide hand-held operation (e.g., a handle to position the ultrasound probe 110) and released down to attach the disposable sterile module 150 with the ultrasound probe 110 to, for example, a person's skin.

The disposable sterile module 150 also optionally includes a sterile probe cable cover 162 for covering the probe cable 118. The sterile probe cable cover 162 may be formed form any material and may be configured, for example, as a flexible sleeve or sheath that is configured to cover at least a portion of the probe cable 118 and having a sterile outside surface.

It should be noted that ring-shaped body 151 may be modified as desired or needed. For example, additional probe contact sections 152 may be provided to support additional ultrasound probes. Also, instead of the ring-shaped body 151, other shaped bodies may be provided as desired or needed, for example, based on the shape of the probe or the region to which the disposable sterile module 150 is to be attached (e.g., part of the body to which the disposable sterile module 150 is to be attached). In one embodiment, a generally rectangular shaped body may be provided to be used with the ultrasound probe 120. However, the ring-shaped body 151 also may be used with the ultrasound probe 120.

Figure 7:
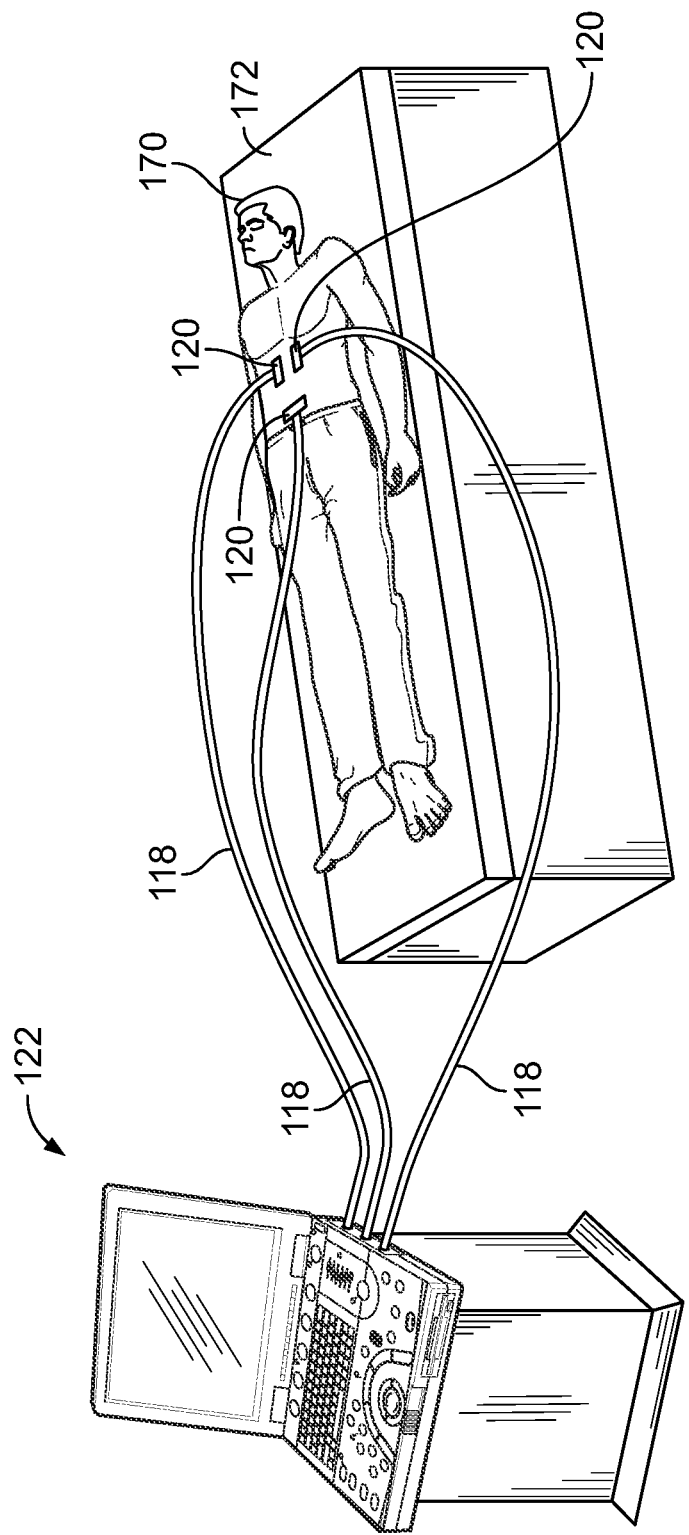
FIG. 7 is a drawing illustrating multiple ultrasound probes having a patch type structure attached to a person to be imaged in accordance with an embodiment of the invention.

Thus, in various embodiments of the invention, one or more of the ultrasound probes described herein may be secured in a fixed position, such as to a region of interest to be imaged. For example, one or more ultrasound probes 120 may be attached to a patient 170 (shown supported on a table 172) as shown in FIG. 7 and connected to the host system 122, which may form part of the ultrasound system 20. The one or more ultrasound probes 120 may be configured as patch type structures (e.g., freely positionable structures that cover a portion of the skin). The ultrasound probes 120 may be attached to the skin of the patient 170, for example, directly using an adhesive material or alternatively using, for example, any type of single use suction device as is known in the medical industry and which may be useful in neonate applications. In some embodiments, the ultrasound probes 120 may be attached to the skin of the patient 170 using the disposable sterile module 150, which may be provided as a single-use kit. Using the disposable sterile module 150, an operator may place one or more ultrasound probes 120 directly on the skin of the patient 170 in one or more regions of interest, secure the ultrasound probe 120 in desired or required positions and orientations using the adhesive and then acquire one or more images of the one or more regions of interest using the host system 122.

It should be noted that more than one ultrasound probe 120 may be positioned to image the same region of interest or different regions of interest. For example, when configured as a patch type structure, using more than one ultrasound probe 120 allows guidance of a catheter past or through a structure, such as the liver, but the end point of the catheter is a distance away that is not easily imaged by the same ultrasound probe 120. As another example, the ultrasound probes 120 configured as patch type structures may be place abdominally, between the ribs, sub-sternally, sub-costally and/or on the back side of a patient, such as adjacent the spine.

Accordingly, with live volumetric data acquisition, a user can perform a procedure (e.g., a guided interventional procedure) while viewing live perpendicular bi-plane images, with the capability to move the plane to a required or desired position using the host system 122. The capability to view live volume rendering of the acquired region without having to move the one or more ultrasound probes 120 is also provided.

At least one technical effect of the various embodiments of the systems and methods described herein include providing a smaller or miniaturized ultrasound probe that allows use of both hands during an ultrasound guided interventional procedure. A disposable sterile module also may be provided that facilitates direct attachment of the ultrasound probe to a patient's skin. The smaller ultrasound probe allows a physician to have both hands free to perform a procedure (e.g., a guided interventional procedure) and allows alternating scanning planes without moving the ultrasound probe. Additionally, volumetric imaging with the various embodiments allows, for example, visualizing the entire vascular tree in a region, for example, using 3D power Doppler (or color Doppler) imaging, to show the physician the vessels in the region of the procedure to avoid hitting the vessels, such as with a needle. The smaller ultrasound probe with lighter weight also allows imaging of very small neonate patients. A flatter configuration for the ultrasound probe also allows the ultrasound probe to be placed under a sheet used for keeping a sterile field in an interventional procedure.

It should be noted that modifications to the various embodiments are contemplated. For example, a miniaturized trackball 182 may be provided on a probe 180 as shown in FIG. 8, and in particular, on a housing 184 of the probe 180. The miniaturized trackball 182 may be about one-fourth the size of a standard track ball (e.g., a ball having a diameter of between about 5 mm and 15 mm). The miniaturized trackball 182 may allow control of, for example, the scanning planes or other user accessible items on the host system 122. In other embodiments, and for example, the scan planes are selected using the host system 122 (shown in FIG. 5) and the miniaturized trackball 182 selects the view planes or volume area, the rendering method and/or the image adjustment parameters. One or more buttons 186, which may be miniaturized or larger, may be provided in addition to or instead of the miniaturized trackball 182.

As another example, a miniaturized touch-pad 192 may be provided on a probe 190 as shown in FIG. 9, and in particular, on a housing 194 of the probe 190. The miniaturized touch-pad 192 may be about one-fourth the size of a standard touch-pad (e.g., a pad having a length and width of between about 10 mm and 20 mm) The miniaturized touch-pad 192 may allow control of, for example, the scanning planes or other user accessible items on the host system 122. In other embodiments, and for example, the scan planes are selected using the host system 122 (shown in FIG. 5) and the miniaturized touch-pad 192 selects the view planes or volume area, the rendering method and/or the image adjustment parameters. One or more buttons 196, which may be miniaturized or larger, may be provided in addition to or instead of the miniaturized touch-pad 192.

Figure 10:
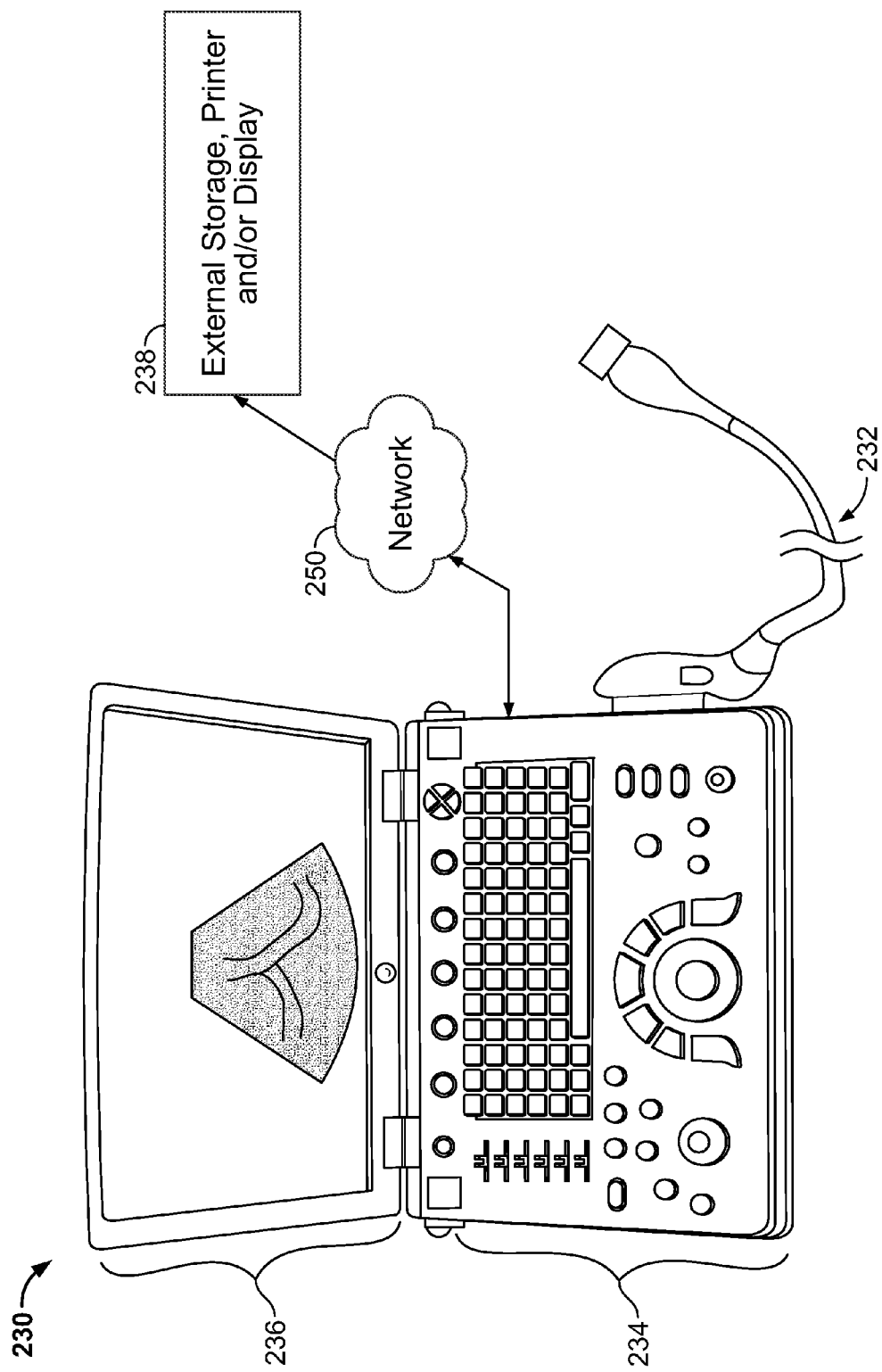
FIG. 10 is a drawing illustrating a miniaturized ultrasound imaging system that may be configured to connect to an ultrasound probe in accordance with various embodiments of the invention.

It also should be noted that the various embodiments may be implemented in connection with different types and kinds of ultrasound systems. For example, as shown in FIG. 10, a 3D-capable miniaturized ultrasound imaging system 230 having a probe 232 may be provided. For example, the probe 232 may be a miniaturized probe as previously described above. A user interface 234 (that may also include an integrated display 236) is provided to receive commands from an operator. As used herein, "miniaturized" means with respect to the ultrasound system 230 that the system is a handheld or hand-carried device or is configured to be carried in a person's hand, pocket, briefcase-sized case, or backpack. For example, the ultrasound system 230 may be a hand-carried device having a size of a typical laptop computer, for instance, having dimensions of approximately 2.5 inches in depth, approximately 14 inches in width, and approximately 12 inches in height. The ultrasound system 230 may weigh about ten pounds, and thus is easily portable by the operator. The integrated display 236 (e.g., an internal display) is also provided and is configured to display a medical image.

The ultrasonic data may be sent to an external device 238 via a wired or wireless network 250 (or direct connection, for example, via a serial or parallel cable or USB port). In some embodiments, the external device 238 may be a computer or a workstation having a display. Alternatively, the external device 238 may be a separate external display or a printer capable of receiving image data from the hand carried ultrasound system 230 and of displaying or printing images that may have greater resolution than the integrated display 236.

Figure 11:
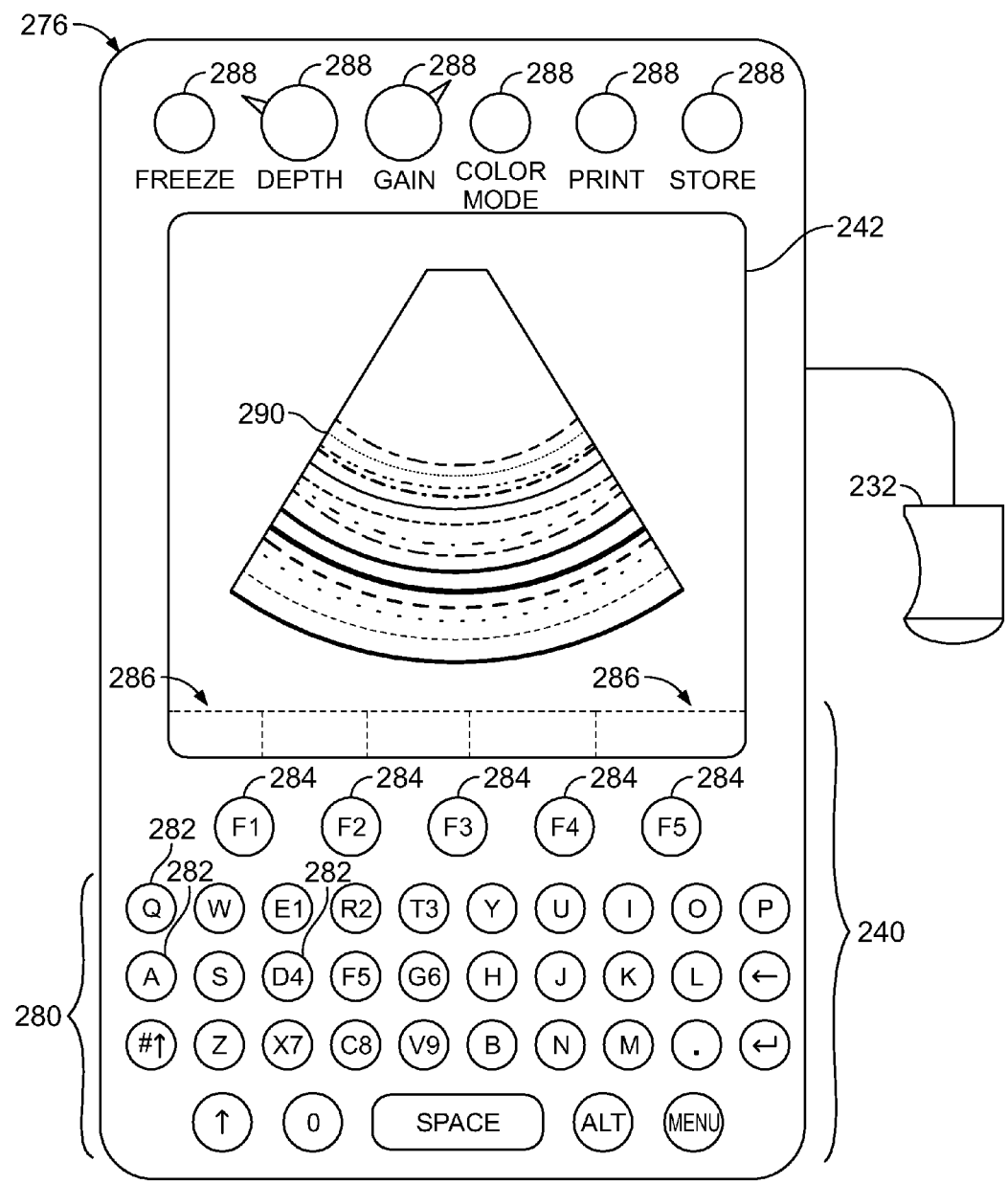
FIG. 11 is a drawing illustrating a hand carried or pocket-sized ultrasound imaging system that may be configured to connect to an ultrasound probe in accordance with various embodiments of the invention.

As another example shown in FIG. 11, a hand carried or pocket-sized ultrasound imaging system 276 may be provided. In the system 276, display 242 and user interface 240 form a single unit. By way of example, the pocket-sized ultrasound imaging system 276 may be a pocket-sized or hand-sized ultrasound system approximately 2 inches wide, approximately 4 inches in length, and approximately 0.5 inches in depth and weighs less than one pound. The display 242 may be, for example, a 320×320 pixel color LCD display (on which a medical image 290 may be displayed in combination with a graphical representation of the probe 232). A typewriter-like keyboard 280 of buttons 282 may optionally be included in the user interface 240. It should be noted that the various embodiments may be implemented in connection with a pocket-sized ultrasound system 276 having different dimensions, weights, and power consumption.

Multi-function controls 284 may each be assigned functions in accordance with the mode of system operation. Therefore, each of the multi-function controls 284 may be configured to provide a plurality of different actions. Label display areas 286 associated with the multi-function controls 284 may be included as necessary on the display 242. The system 276 may also have additional keys and/or controls 288 for special purpose functions, which may include, but are not limited to "freeze," "depth control," "gain control," "color-mode," "print," and "store."

Figure 12:
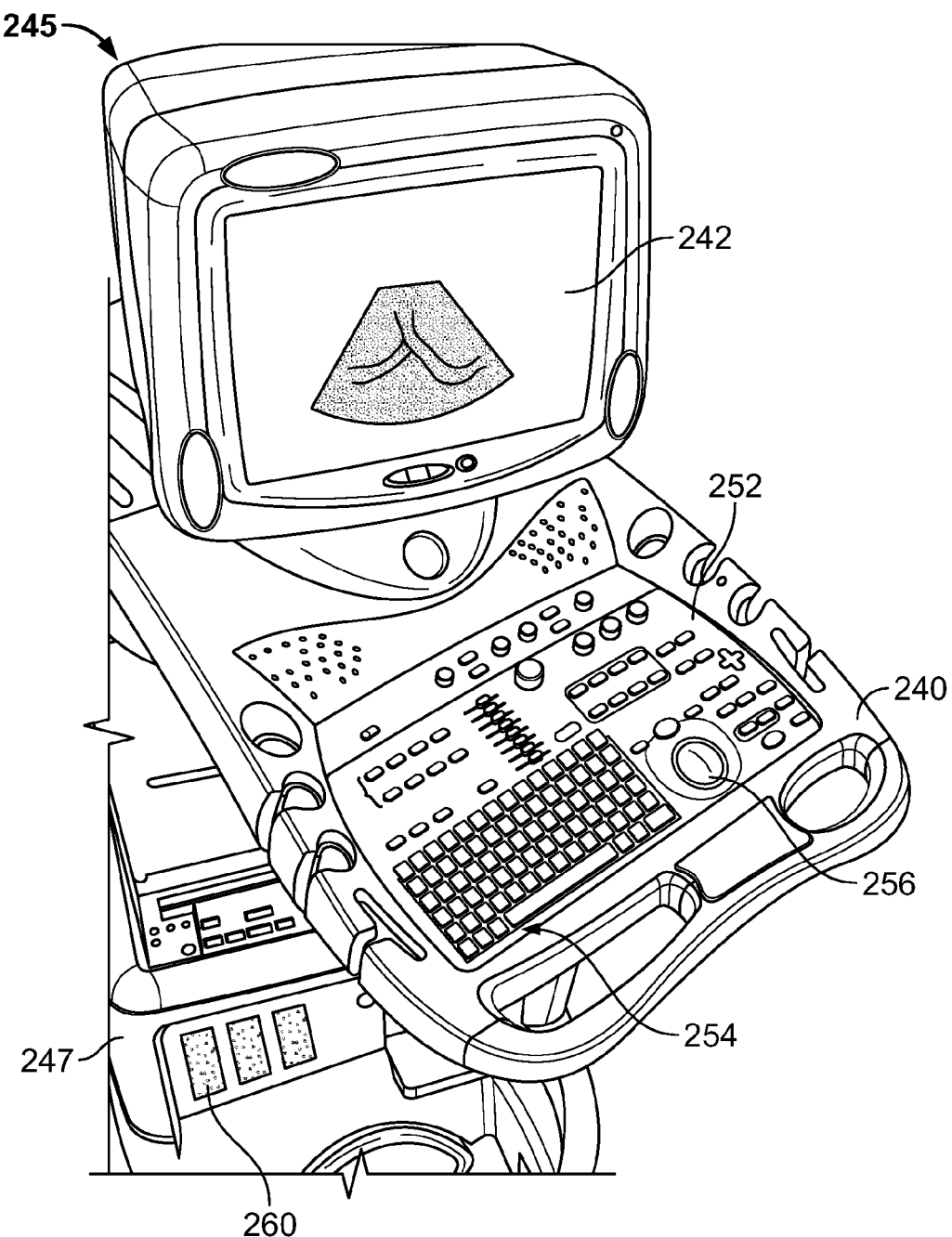
FIG. 12 is a drawing illustrating a console-based ultrasound imaging system provided on a movable base that may be configured to connect to an ultrasound probe in accordance with various embodiments of the invention.

As another example shown in FIG. 12, a console-based ultrasound imaging system 245 may be provided on a movable base 247. The portable ultrasound imaging system 245 may also be referred to as a cart-based system. A display 242 and user interface 240 are provided and it should be understood that the display 242 may be separate or separable from the user interface 240. The user interface 240 may optionally be a touchscreen, allowing the operator to select options by touching displayed graphics, icons, and the like.

The user interface 240 also includes control buttons 252 that may be used to control the portable ultrasound imaging system 245 as desired or needed, and/or as typically provided. The user interface 240 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 254 and trackball 256 may be provided. The system 245 has at least one probe port 260 for accepting probes.

Figure 13:
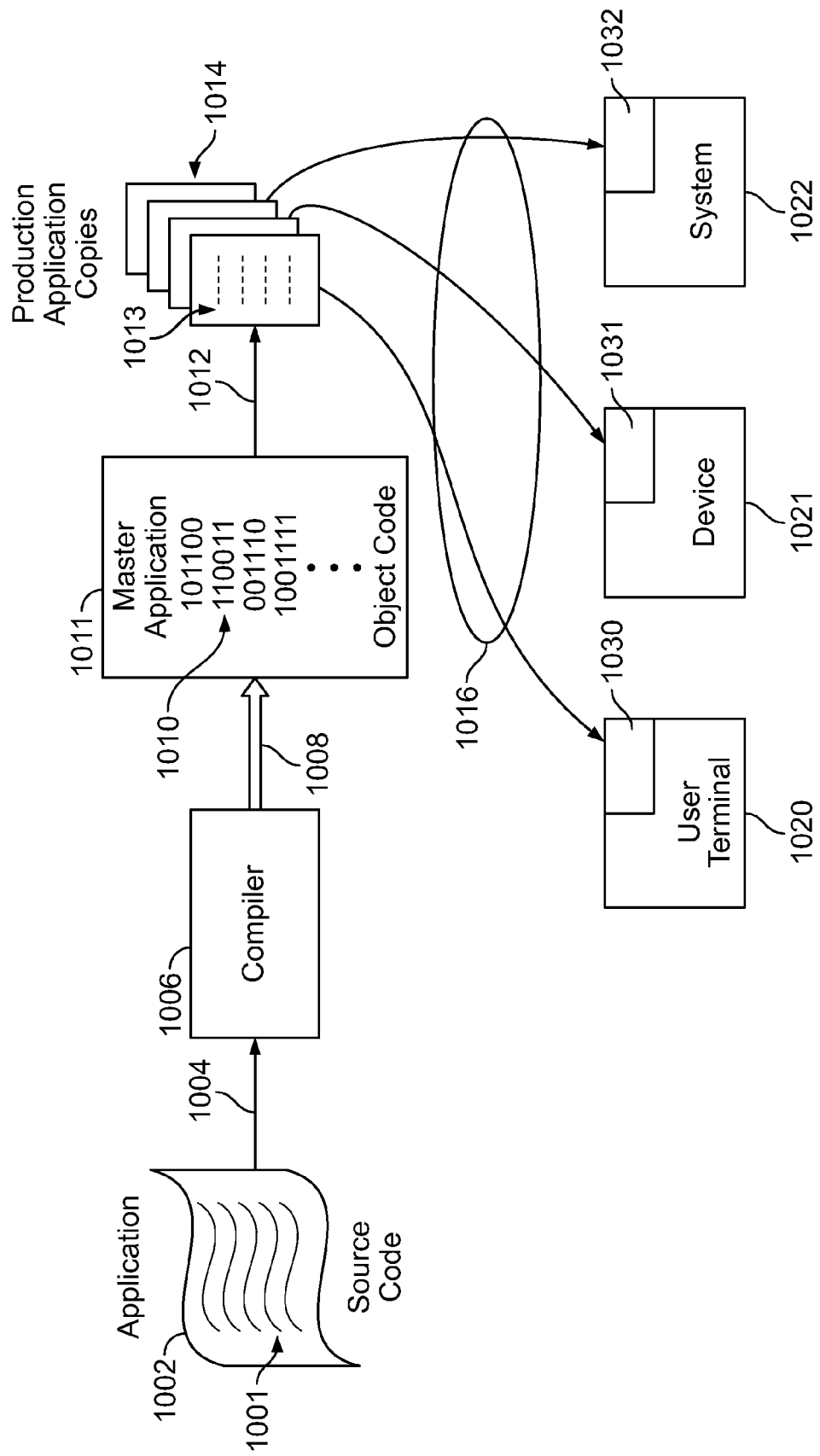
FIG. 13 is a block diagram of exemplary manners in which embodiments of the invention may be stored, distributed and installed on computer readable medium.

FIG. 13 is a block diagram of exemplary manners in which embodiments of the present invention may be stored, distributed and installed on computer readable medium. In FIG. 13, the "application" represents one or more of the methods and process operations discussed above.

As shown in FIG. 13, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous times, as denoted by path 1012, to produce production application copies 1013 that are saved on separate production computer readable medium 1014. The production computer readable medium 1014 is then conveyed, as denoted by path 1016, to various systems, devices, terminals and the like. In the example of FIG. 13, a user terminal 1020, a device 1021 and a system 1022 are shown as examples of hardware components, on which the production computer readable medium 1014 are installed as applications (as denoted by 1030-1032).

The source code may be written as scripts, or in any high-level or low-level language. Examples of the source, master, and production computer readable medium 1002, 1011 and 1014 include, but are not limited to, CDROM, RAM, ROM, Flash memory, RAID drives, memory on a computer system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011 or 1014 between two geographic locations. The paths 1004, 1008, 1012 and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, inter-continental and the like.

The operations noted in FIG. 13 may be performed in a widely distributed manner world-wide with only a portion thereof being performed in the United States. For example, the application source code 1001 may be written in the United States and saved on a source computer readable medium 1002 in the United States, but transported to another country (corresponding to path 1004) before compiling, copying and installation. Alternatively, the application source code 1001 may be written in or outside of the United States, compiled at a compiler 1006 located in the United States and saved on a master computer readable medium 1011 in the United States, but the object code 1010 transported to another country (corresponding to path 1012) before copying and installation. Alternatively, the application source code 1001 and object code 1010 may be produced in or outside of the United States, but production application copies 1013 produced in or conveyed to the United States (e.g. as part of a staging operation) before the production application copies 1013 are installed on user terminals 1020, devices 1021, and/or systems 1022 located in or outside the United States as applications 1030-1032.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

The various embodiments and/or components, for example, the host system, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound probe comprising:
a housing having a generally rectangular cross-section, the housing defining a patch structure configured to attach to a person in at least one of a fixed position or orientation on the person;
a linear transducer array within the housing; and
a micro-motor within the housing and configured to mechanically move the linear transducer array to acquire volumetric data to provide ultrasound guidance of procedures.

2. An ultrasound probe in accordance with claim 1 further comprising a generally cylindrical housing and wherein the linear transducer array is configured to rotate about a longitudinal axis of the generally cylindrical housing.

3. An ultrasound probe in accordance with claim 1 having one of a weight and size to allow attachment to a person.

4. An ultrasound probe in accordance with claim 3 wherein the attachment is to a portion of a skin of the person.

5. An ultrasound probe in accordance with claim 1 further comprising at least one of a miniaturized trackball or miniaturized touch-pad on a housing encasing the linear transducer array and the micro-motor.

6. An ultrasound probe in accordance with claim 1 further comprising at least one button on a housing encasing the linear transducer array and the micro-motor.

7. An ultrasound probe in accordance with claim 1 wherein the housing has a face that attaches to the person and wherein the linear transducer array rotates normal to the face.

8. An ultrasound probe in accordance with claim 1 wherein the housing has a front face that attaches to the person and sides adjacent the front face and together with a back face form the patch structure, and wherein the linear transducer array rotates normal to one of the sides.

9. An ultrasound probe in accordance with claim 1 further comprising at least one multiplexer board having an integrated multiplexing chip connected to the linear transducer array.

10. An ultrasound probe in accordance with claim 1 wherein the linear transducer array is configured to mechanically move to acquire live perpendicular bi-plane images.

11. An ultrasound probe in accordance with claim 1 wherein the linear transducer array is configured to mechanically move to perform color Doppler imaging of vessels within a region of a procedure.

12. An ultrasound probe in accordance with claim 1 wherein the housing comprises a dry chamber and a wet chamber, wherein the micro-motor is within the dry chamber and the linear transducer array is in the wet chamber, and a drive connecting the micro-motor to the linear transducer array through a fluid seal between the wet and dry chambers.

13. An ultrasound probe in accordance with claim 1 wherein the ultrasound probe weighs less than 100 grams.

14. An ultrasound probe in accordance with claim 1 wherein the housing has a volume of less than 15,000 $mm^3$.

* * * * *